United States Patent [19]

Palti

[11] Patent Number: 4,660,566
[45] Date of Patent: Apr. 28, 1987

[54] METHOD AND APPARATUS FOR THE NON-INVASIVE MONITORING OF ARTERIAL BLOOD PRESSURE WAVES

[75] Inventor: Yoram Palti, Haifa, Israel

[73] Assignee: Fidelity Medical, Inc., Millburn, N.J.

[21] Appl. No.: 802,024

[22] Filed: Nov. 25, 1985

Related U.S. Application Data

[63] Continuation-in-part of Ser. No. 592,253, Mar. 22, 1984, abandoned, which is a continuation-in-part of Ser. No. 429,679, Sep. 30, 1982, abandoned.

[30] Foreign Application Priority Data

May 13, 1983 [IL] Israel ....................................... 68685
Nov. 15, 1983 [IL] Israel ....................................... 70243

[51] Int. Cl.⁴ .............................................. A61B 5/02
[52] U.S. Cl. .................................................. 128/677
[58] Field of Search ..................... 128/677, 680–683, 128/687–690

[56] References Cited

U.S. PATENT DOCUMENTS

| | | | |
|---|---|---|---|
| 3,118,440 | 1/1964 | Dobbeleer | 128/679 |
| 3,527,197 | 9/1970 | Ware | 128/662 |
| 3,552,381 | 1/1971 | Burns et al. | 128/683 |
| 4,331,154 | 5/1982 | Broadwater et al. | 128/677 |
| 4,343,314 | 8/1982 | Sramek | 128/660 |
| 4,406,289 | 9/1983 | Wesseling et al. | 128/690 X |

OTHER PUBLICATIONS

Geddes, L. A., "The Direct and Indirect Measurement of Blood Pressure", Chapter 2, pp. 70–83, Yearbook Publ. Inc., Chicago, 1970.

Primary Examiner—Kyle L. Howell
Assistant Examiner—Francis J. Jaworski
Attorney, Agent, or Firm—Leiberman, Rudolph and Nowak

[57] ABSTRACT

A method and apparatus for the non-invasive monitoring of the arterial blood pressure of a subject are described in which a plurality of discretely-spaced single-polarity pressure pulses, each having a duration which is a fraction of the duration of the subject's blood pressure pulse, are applied to a local, discrete, external point of the subject overlying an artery to effect either a blocking or unblocking condition of the artery. When the condition is detected, the instant value of the applied pressure pulse is measured to thereby provide a measurement of the subject's blood pressure.

31 Claims, 25 Drawing Figures

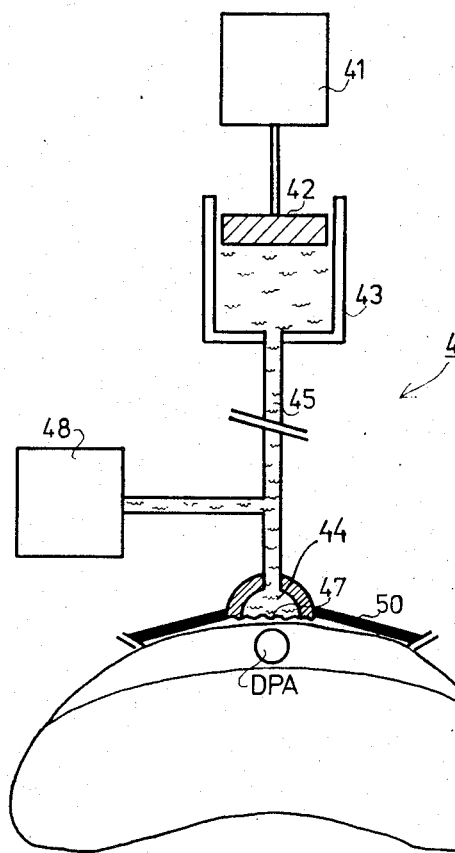
FIG. 4
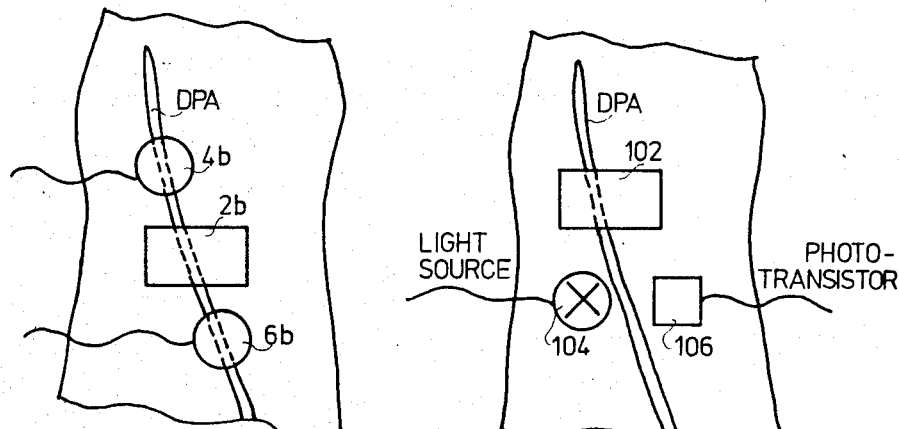
FIG. 5b
FIG. 8

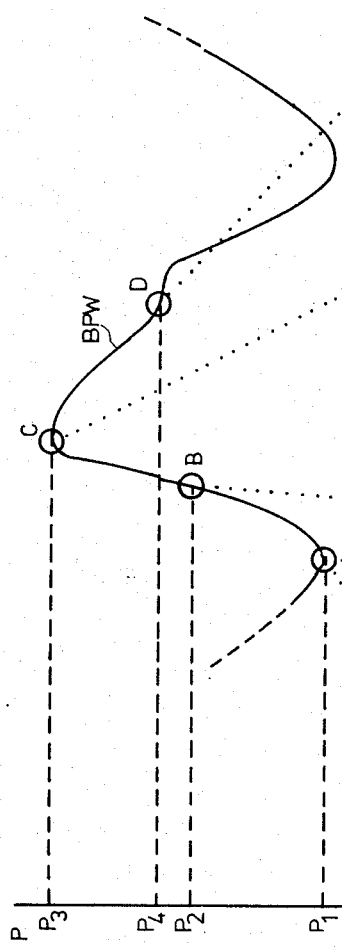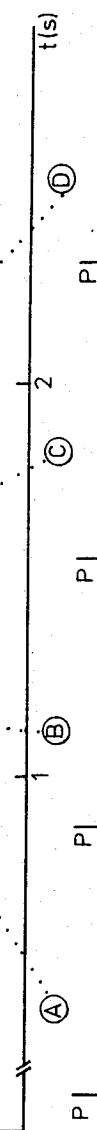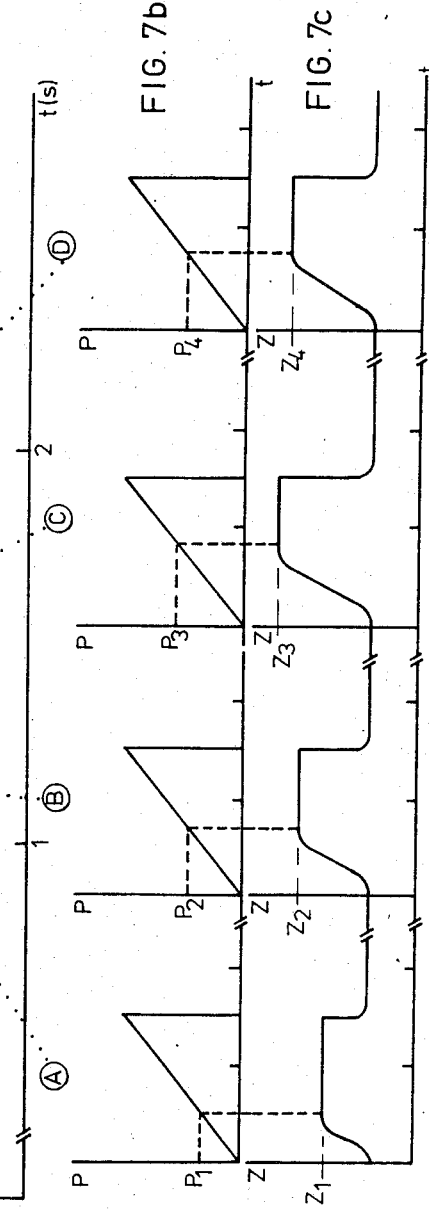
FIG. 7a
FIG. 7b
FIG. 7c

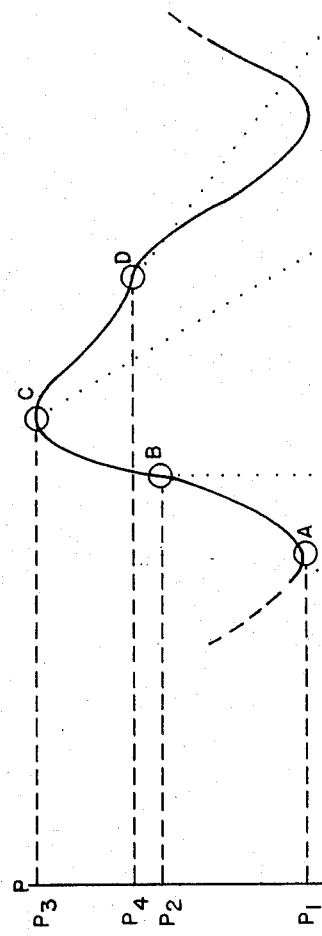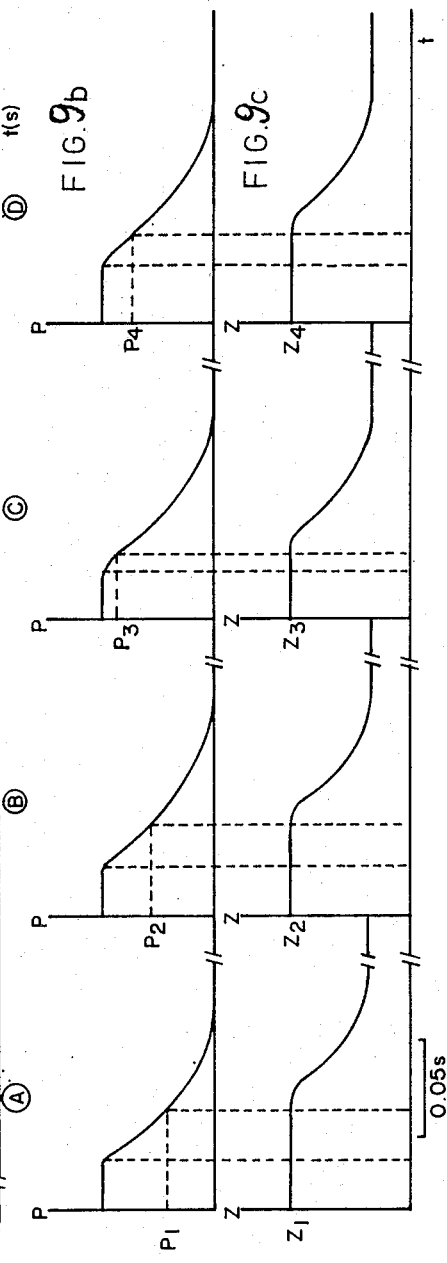
FIG 9a
FIG.9b
FIG.9c

METHOD AND APPARATUS FOR THE NON-INVASIVE MONITORING OF ARTERIAL BLOOD PRESSURE WAVES

RELATED APPLICATION

The present application is a continuation-in-part of patent application Ser. No. 592,253 filed Mar. 22, 1984 and now abandoned, which in turn is a continuation-in-part of patent application Ser. No. 429,679 filed Sept. 30, 1982, now abandoned.

BACKGROUND OF THE INVENTION

The present invention relates to a novel method and apparatus for the non-invasive monitoring of arterial blood pressure waves.

The arterial blood pressure is widely used for assessing the status of a subject's cardiovascular system, and its measurement is one of the most common clinical procedures practiced in all levels of medicine for both diagnostic and prognostic purposes. The direct measurement of blood pressure involves the introduction of a catheter in an artery of the body. Because of its invasive nature, this technique is usually restricted to situations where it is essential, for example, in certain surgical procedures and in the intensive care of critically ill patients. Accordingly, most blood pressure measurements are made indirectly by the use of a cuff.

The sphygmomanometric auscultatory method, which was first described and used about 80 years ago, is by far the one most commonly used today. This method is based on the application of an external pressure around an artery (in the arm), and the monitoring of the mechanical pulsations, thus modified, at a point below the constricted area. The pressure is applied by inflating a rubber bladder surrounded by a cuff placed on the arm. The pressure is monitored by a mercury or annular manometer, while the pulsations are monitored by a stethoscope. Automatic measurement devices use the same principle with the exception that the pulsations are monitored by other means, such as a microphone, piezoelectric sensor, photoelectric sensor, more sophisticated movement detectors based on the Doppler principle, etc. By recognizing specific changes in the nature of the mechanical vibrations or sounds, the operator or automated device can determine the systolic, diastolic, and the mean blood pressure in the artery.

The above known indirect measurement techniques suffer from a number of inherent drawbacks, including the following:

1. The error in the determination of the systolic and diastolic pressures, which error commonly exceeds +−10 mm Hg, is a function of the ability and experience of the operator, the relationship between the arm diameter and cuff dimensions, the pressure value, the degree of peripheral vascular sclerosis, etc.
2. The change in sound, by means of which the end point or actual pressures are being determined, are difficult to detect.
3. Shortly after the cuff is inflated, pain ensues in the extremity.
4. Cuffs of different sizes should be used for different patients.
5. The procedure of applying the cuff is inconvenient.
6. The method cannot be used for continuous blood pressure measurements and is inconvenient even for infrequent pressure determinations.
7. The method can hardly be used for pressure determination while the patient is pursuing his normal activities.
8. The method requires trained personnel to carry out the measurement.
9. The method is inconvenient for self use.
10. The method is not easy to automate.
11. The measurement procedure requires a relatively long time, e.g., 30–60 seconds.

BRIEF SUMMARY OF THE INVENTION

An object of the present invention is to provide a novel method and apparatus for the non-invasive monitoring of arterial blood pressure waves. Another object of the invention is to provide a bracelet particularly useful in the novel method and apparatus.

According to a broad aspect of the present invention, there is provided a method and apparatus for the non-invasive monitoring of the arterial blood pressure wave of a subject, characterized in: applying a plurality of discretely spaced single-polarity pressure pulses, each having a duration which is a fraction of the duration of the subject's blood pressure pulse, to a local, discrete, external point of the subject overlying an artery to effect either a blocking or unblocking condition of the artery; detecting when said condition in the artery occurs; and measuring the instant value of the applied pressure pulse when the condition is detected to thereby provide a measurement of the subject's blood pressure.

It has been found that a measurement of the arterial blood pressure can be provided by measuring the value of the local pressure not only when blocking (occlusion) is detected, but also when the unblocking of an occluded artery occurs according to the above described technique.

According to further features of the invention, the novel method and apparatus is further characterized by monitoring the subject's complete arterial blood pressure pulse; and timing a least two of the applied pressure pulses to coincide with the maximum and minimum values of the subject's blood pressure pulse to thereby provide a measurement of the systolic and diastolic values of the subject's blood pressure.

According to a further feature, more than two single-polarity pulses are applied to coincide with other values of the subject's complete arterial blood pressure pulse to thereby provide a continuous measurement tracing the subject's complete blood pressre wave.

The invention provides a number of important advantages over the conventional non-invasive cuff techniques in common use today. Thus, the novel technique may be used for measuring systolic blood pressure, and diastolic blood pressure; and by providing a plurality of measurements during a single blood pressure pulse, it can also be used for indicating the whole blood pressure wave. In addition, highly trained personnel are not required, and the results produced are less dependent on the skill and experience of the operating personnel. Further, since the pressure is applied as a localized pressure point, rather than as an annular pressure by a cuff which surrounds the subject's extremity, the blood pressure measurement may be more conveniently made even by the patient himself. Moreover, the device may be worn by the patient so as to provide a continuous measurement without restricting his normal movements or his normal activities. Still further, the actual measurement takes a very short time, in the order of a few seconds, a small fraction of the time required in the conventional method.

It has been previously proposed to provide a non-invasive blood pressure measurement by using a cuff connected to a pump which cyclically varies the cuff pressure in a sinusoidal manner from above systolic to below diastolic levels at a relatively fast rate compared to to the heartbeat rate. See for example Sramek U.S. Pat. No. 4,343,314 of Aug. 10, 1982. The use of a cuff, however, in that technique does not provide the above-discussed advantages of the novel method using local pressure points. Moreover, there are a number of very important advantages in the novel method using discretely-spaced single-polarity pulses, over the sinusoidal oscillations described in that patent.

Thus, the pulses used in the present novel technique may be controlled so as to have a brief pulse duration, a rapid rate of change, and a long interval between pulses. These characteristics provide a number of very important advantages including the following: The individually controlled pulses of the novel technique permit precise synchronization of each pulse with the subject's blood pressure pulse so as to allow optimum monitoring of the systolic and diastolic blood pressure, as well as all points in between. In addition, by individually controlling the intervals between the pulses, the pulse train can be optimally adjusted according to the mechanical delays and response time of the tissue so as to better permit the tissue to return to its original condition before the next pulse is applied; this is not possible with the sinusoidal oscillations of the previously known technique. Further, by controlling the pulses so as to be brief in duration and to have a rapid rate of change, the novel technique permits higher rates of measurement to be made for determining not only the systolic and diastolic values, but also other discrete points, thereby more accurately tracing the blood pressure waves.

Further features and advantages of the invention will be apparent from the description below.

BRIEF DESCRIPTION OF THE DRAWINGS

The invention is herein described, by way of example only, with reference to the accompanying drawings, wherein:

FIGS. 3 and 4 illustrate two further forms of pressure applicators that may be used;

FIGS. 5a and 5b illustrate two other arrangements for applying the impedance-measuring electrodes to the patient;

FIGS. 7a–7c are graphs illustrating how the systolic, diastolic, or whole blood pressure wave may be measured in accordance with the present invention;

FIG. 8 illustrates another embodiment of the invention wherein the detected property change, upon the application of the local pressure, is a change in the photo-transmittance or photo-reflectance of the subject's external area in the vicinity of the occluded artery.

FIGS. 9a–9c are graphs corresponding to FIGS. 7a–7c, but illustrating how the systolic, diastolic, or whole blood pressure wave may be measured by a decreasing pressure pulse applied to the external area of the subject overlying the artery;

DESCRIPTION OF PREFERRED EMBODIMENTS

The Embodiment of FIGS. 1–7c

The embodiment of the invention illustrated in FIGS. 1–7c is based on the detection of the change in the electrical impedance of the external area of the subject overlying the artery occluded by the application of the local pressure. In this embodiment, the local pressure is applied to the dorsalis pedis artery on the topside of the foot close to the ankle. It will be appreciated, however, that this local pressure could also be applied to other arteries, for example, the radial artery at the base of the hand.

Figure 1:
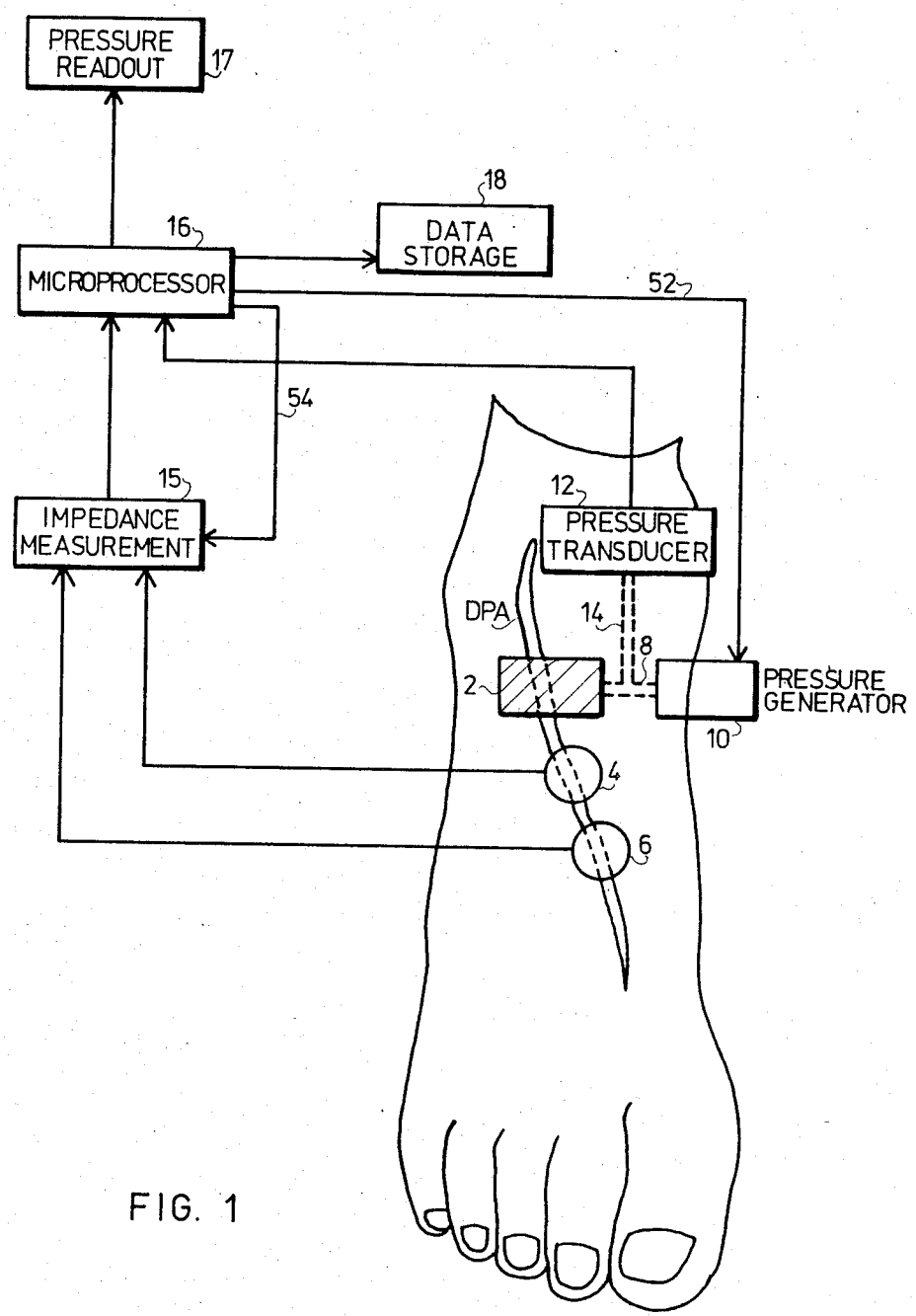
FIG. 1 schematically illustrates one form of apparatus constructed in accordance with the present invention for the non-invasive monitoring of the arterial blood pressure waves of a subject.

As shown in FIG. 1, the local external pressure is applied by a pressure applicator, schematically indicated at 2, to the dorsalis pedis artery DPA, and the change in electrical impedance is detected by a pair of electrodes 4 and 6 overlying the arterly laterally of the pressure applicator 2. The two electrodes 4, 6 may each be about 0.5–1 cm. in diameter and may be spaced about 1 cm apart; they should make good electrical contact with the skin.

Pressure applicator 2 is coupled, by a coupling schematically indicated at 8, to a pressure generator 10. Coupling 8 may be a rigid mechanical coupling, as to be described below in connection with FIG. 2, or it may be a liquid coupling as to be described below in connection with FIGS. 3 and 4. The pressure transmitted from the pressure generator 10 to the pressure applicator 2 is also applied to a pressure transducer 12 via another coupling 14 communicating with coupling 8.

Electrodes 4 and 6 are connected to an electric impedance measuring circuit 15 whose output is fed to a processor 16. The latter processor also receives the output from pressure transducer 12 and, after processing the information as will be described more particularly below, outputs this information to a pressure readout device 17, preferably of the digital type. Processor 16 may also output information to a data storage device 18 for subsequent readout, display, or further processing.

Figure 2:
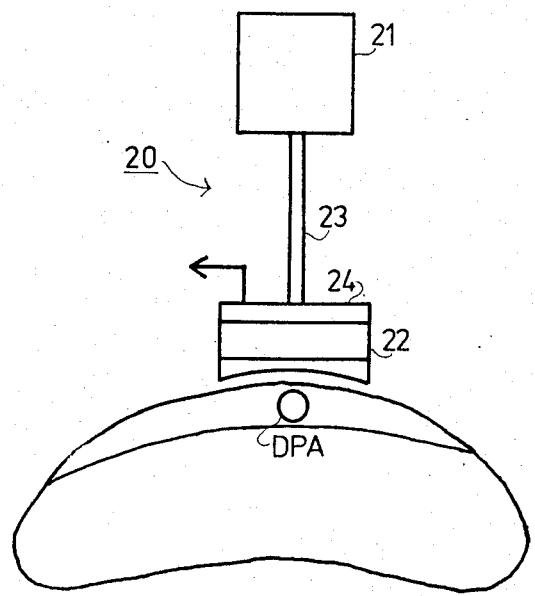
FIG. 2 schematically illustrates one form of pressure applicator which may be used for applying the local pressure to the artery of the subject.

FIG. 2 illustrates one form of pressure applicator, therein designated 20, which may be used for applying the local pressure to occlude the artery. Thus, pressure applicator 20 includes a driver device 21, which may be an electo-magnetic type reciprocating plunger; a rigid foot 22 applied to the subject's skin over the artery; a rigid coupling 23 between the driver 21 and the rigid foot 22; and a pressure or force transducer 24, such as the piezo-electric crystal, for measuring the force applied by rigid foot 22 to the subject's skin.

Figure 3:
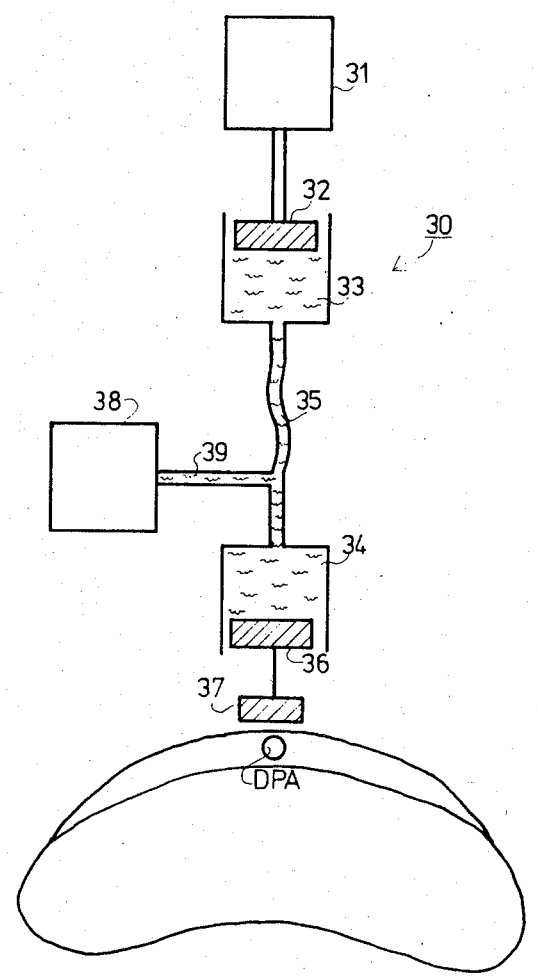

FIG. 3 illustrates another pressure applicator, therein designated 30, including a liquid coupling between the driving device and the driven member applied to the patient's skin. Thus, the pressure applicator 30 in FIG. 3 includes a plunger, e.g., electromagnetically-driven; a piston 32 driven by plunger 31 and movable within a cylinder 33; a second cylinder 34 connected to a cylinder 33 by a liquid conduit 35; a second piston 36 movable within cylinder 34; and a foot 37 mechanically coupled to piston 36. The pressure applicator 30 in FIG. 3 also includes a pressure transducer 38 which, in this case, is coupled to liquid conduit 35 via another conduit 39. Thus, the pressure produced by the displacement of piston 32 within cylinder 33 is transmitted, via the liquid coupling 35, to piston 36 movable within cylinder 34, and thereby to the patient's skin via the foot 37 coupled to piston 36. This pressure is also transmitted to the pressure transducer 38 via liquid conduit 39.

FIG. 4 illustrates another pressure applicator, generally designated 40, which may be used and which also includes a liquid coupling between the driving device and the driven member applied to the subject's skin.

Thus, the pressure applicator 40 shown in FIG. 4, also includes a piston driver 41, a piston 42 movable within a cylinder 43, a liquid conduit 45, and a pressure transducer 48, all corresponding to elements 31, 32, 33, 35 and 38, respectively, in the FIG. 3 embodiment. In the FIG. 4 embodiment, however, the driven member applied to the patient's skin is in the form of a membrane 47 closing one end of a a rigid chamber 44 of semi-circle configuration; the opposite end of chamber 44 communicates with the liquid conduit 45. Thus, the pressure applied by the plunger driver 41 is transmitted via the liquid within conduit 45 and chamber 44 to the flexible membrane 47, and thereby to the subject's skin overlying the artery to be occluded.

The pressure applicator of FIG. 4 also includes a strap or bracelet 50 which may be applied to the ankle of the patient for retaining the pressure applicator chamber 44 and the membrane 47 in place on the subject's foot. Thus, the driving elements 41–43 may be worn by the user in a convenient place, such as in a pocket or holster, and may be connected to chamber 44 by a flexible tubing 45, thereby permitting the device to be conveniently worn by the user without interfering with his normal activities.

Figure 5A:
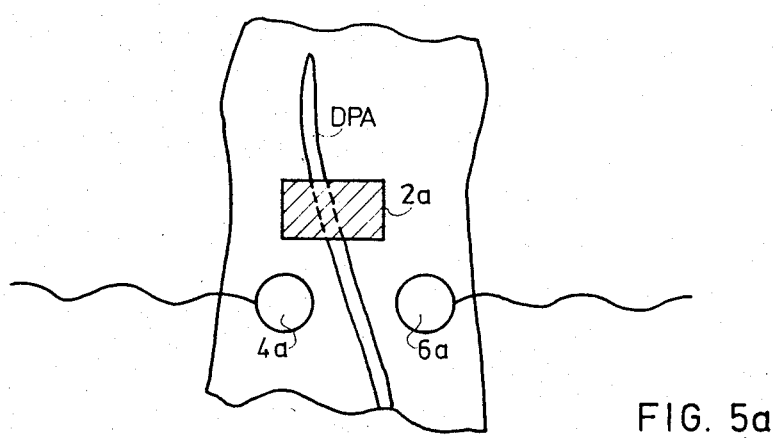

Whereas FIG. 1 illustrates the two electrodes 4, 6 applied over the artery DPA laterally of the pressure applicator 2, it will be appreciated that they could be applied in other locations. FIG. 5a, for example, illustrates the two electrodes, therein designated 4a, 6a, as straddling the artery DPA; and FIG. 5b illustrates the two electrodes, therein designated 4b, 6b as overlying the artery but straddling the pressure applicator 2b.

Figure 6:
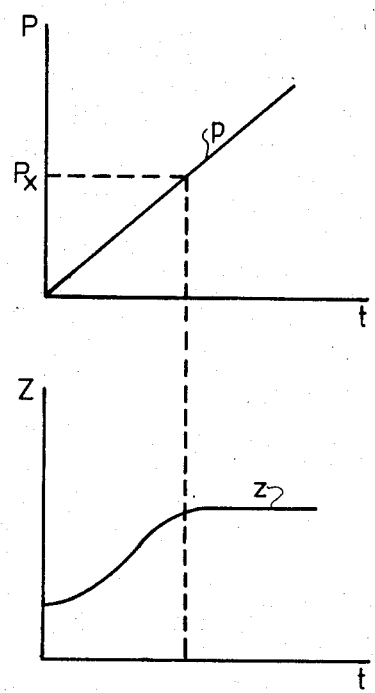
FIG. 6 is a graph illustrating the correlation between the measured impedance and the momentary pressure in the artery as induced by the pressure applicator.

FIG. 6 illustrates the correlation between the impedance ("z," lower curve) and the momentary pressure ("p," upper curve) applied to the artery by the pressure applicator. Thus, as this pressure increases, the impedance between the electrodes increases in a sigmoidal manner, and reaches a plateau the moment the artery is occluded by the pressure applicator. The applied pressure at the instant of occlusion is the blood pressure at that instant.

FIGS. 7a–7c illustrate how this impedance change, indicating the instant of occlusion, can be used for determining the blood pressure at any point of the blood pressure wave, provided that the time it takes the pressure applied by the applicator to reach an occluding value is short with respect to the duration of the blood pressure wave.

Thus, FIG. 7a illustrates a blood pressure wave BPW in which the momentary pressure is to be measured at points A, B, C, and D of the complete wave. Point A represents the diastolic blood pressure; point C represents the systolic blood pressure; and points B and D are arbitrary intermediate points.

It will be seen from FIGS. 7a–7c that when the pressure applicator is actuated at point A of the blood pressure wave (FIG. 7a), the applied pressure is $p_1$ (FIG. 7b) when the detected impedance reaches the plateau $z_1$ (FIG. 7c) which occurs at the instant of occlusion; the measured pressured $p_1$ at this instant of occlusion, is the momentary blood pressure at point ("A") of the blood pressure wave. In a similar manner, when the pressure applicator is actuated at points B, C, and D of FIG. 7a, the impedance will reach plateaus of $z_2$, $z_3$, and $z_4$ (FIG. 7c), respectively, to signify the momentary blood pressures $p_2$, $p_3$, and $p_4$ (FIG. 7b), respectively.

Thus, by controlling the pressure applicator to apply the local pressure at the proper point of the blood pressure wave, the momentary pressure at that point of the wave can be determined by measuring the impedance at that particular instant. The local pressure can be applied as a series of individual short-duration pulses over the complete blood pressure wave to thereby provide an indication of the whole wave. Alternatively, the pressure pulses can be applied at preselected points of the blood pressure wave, and can be individually synchronized, for example, with the blood pressure wave by piezoelectric or photoelectric means. The pressure transducer for measuring the pressure exerted by the driven member is contact with the subject's skin should have the appropriate frequency response. The pressure applicator and the impedance measuring circuit may be controlled by the processor 16 in FIG. 1, as shown schematically by control lines 52 and 54. Processor 16 may be located at a distance from the measurement point and can process the information received by it so as to produce a measurement of the momentary pressure as a function of time. This information can be displayed graphically, preferably digitally, by the readout device 17, or can be stored in storage unit 18 for subsequent readout, display, or further processing.

The Embodiment of FIG. 8

While a close correlation has been found to exist between the change in impedance and the instant of occlusion as a result of the application of the local pressure, a correlation has also been found to exist between the instant of occlusion and a change in photo-transmittance or photo-reflectance produced at the site as a result of the application of the local pressure. FIG. 8 illustrates an arrangement for monitoring the change of this property resulting from the application of the local pressure. Thus, in the arrangement illustrated in FIG. 8, the pressure applicator, generally designated 102, is applied to the artery DPA as in FIG. 1, except that the occlusion of the artery as a result of this application of local pressure is detected by photometric means, including a light source 104 located on one side of the artery, and a photo-sensitive element 106 located on the opposite side of the artery. Light source 104 and photo-sensitive element 106 can be arranged such that the latter element detects either the light transmitted through the respective portion of the subject's skin, ore light reflected by it, to provide an indication of the momentary pressure at the instant of the artery occlusion by the pressure applied by the applicator 102. In all other respects, the system could include the same arrangements as described earlier for applying the localized pressure, and for processing the information produced thereby.

The Embodiment of FIGS. 9-12

Whereas the above-described technique provides a measurement of the arterial blood pressure by detecting when the occlusion of the artery occurs upon applying individual pulses increasing with time to the external area overlying the artery, it has also been found that a relatively accurate measurement of the arterial blood pressure may be provided by detecting when the unblocking of an occluded artery occurs by applying pulses decreasing in time to the external area overlying the artery. The latter technique is described below with reference to FIGS. 9a-12 of the drawings.

Thus, the correlation between the impedance and the momentary pressure applied to the artery by the pressure applicator (as illustrated in FIG. 6) also applies in the technique of FIGS. 9a-12, but in an inverse manner. That is, in the technique of FIGS. 9a-12 the pressure is applied to the artery and is then interrupted or released so as to decrease, rather than to increase, with time. The impedance value therefore follows a down-going sigmoidal curve, rather than an up-going sigmoidal curve as in the system illustrated in FIGS. 1-8.

FIGS. 9a-9c illustrate the foregoing relationships in the latter technique, and particularly how the impedance change, indicating the instant of unblocking of the occluded artery, can be used for determining the blood pressure at any point of the blood pressure wave, provided that the time of interruption of the pressure applied to the artery to unblock it is short with respect to the duration of the blood pressure wave.

Thus, FIG. 9a illustrates a blood pressure wave BPW which is identical to that in FIG. 7a of the technique of FIGS. 1-8. In this case, however, points A, B, C, and D of the complete wave represent the points of the blood pressure wave in which the applied occluding pressure is to be interrupted so as to measure the blood pressure at these points: Point A represents the diastolic blood pressure; point C represents the systolic blood pressure; and points B and D are arbitrary intermediate points.

It will be seen that when the pressure indicator is interrupted at point A of the blood pressure wave (FIG. 9a), the applied pressure is $p_1$ (FIG. 9b) at the moment that the detected impedance begins to descend from the plateau $Z_1$ (FIG. 9C), which occurs at the instant of unblocking of the occluded artery. The measured pressure $p_1$ at this instant is the momentary blood pressure at point A of the blood pressure wave illustrated in FIG. 9a. In a similar manner, when the pressure continuously applied by the pressure applicator is interrupted at points A, C, and D of FIG. 9a, the impedances at plateaus $z_2$, $z_3$, and $z_4$ will also begin to descend at the points shown in FIG. 9c, to provide measurements of the momentary blood pressure $p_2$, $p_3$ and $p_4$, respectively.

Another modification in the method and apparatus described in the technique of FIGS. 1-8 relates to the manners of applying and then releasing the pressure for purposes of first occluding and then unblocking the artery. Thus, it was found that in a number of body areas chosen for blood pressure measurement in accordance with the technique of the above-described FIGS. 1-8, shunting of the blood flow occurred with respect to the artery being occluded. This resulted in a back pressure and back-flow of blood into the occluded artery, which produced errors in the determination of the blood pressure.

The technique of FIGS. 9a-12 also improves the pressure applicator system for minimizing or eliminating this error caused by the shunting of the blood flow to other arteries. For this purpose, the pressure applicator includes, not a single plunger as in the above-cited patent application, but rather a plurality of plungers, preferably three (or more) arranged in a line along the artery being occluded and controlled according to a predetermined sequence. FIGS. 10a-10e illustrate a preferred sequence with respect to a pressure applicator system including three plungers, namely: plunger 202b, which is the center pressure applicator; plunger 202a, which is the proximal pressure applicator (i.e., the end applicator proximate to the subject's heart); and plunger 202c, which is the distal applicator (i.e., the end applicator distant from the subject's heart). The impedance is measured by electrodes, indicated at 204 and 206, underlying the central plunger 202b.

Figure 10A:
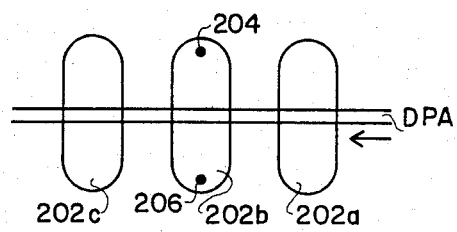
FIGS. 10a–10e are diagrams illustrating a preferred sequence of applying and releasing the pressure while utilizing three pressure-applicators, rather than a single pressure applicator.

A preferred cycle for activating the three plungers is illustated in FIGS. 10a-10e, starting with the condition illustrated in FIG. 10a (phase 1) wherein all the plungers are in their released, non-pressurized condition. Thus, in phase 2 (FIG. 10b), the pressure to the center plunger 202b is applied; in phase 3 (FIG. 10c), the pressure to the two end plungers 202a, 202c, is applied; in phase 4 (FIG. 10d), the pressure to the center plunger 202b is released; and in phase 5 (FIG. 10e), the pressure to the proximal end plunger 202a (proximate to the heart) is released in a controlled manner while the values of pressure and impedance at the center plunger 202b are measured to detect when the unblocking of the artery occurs. The cycle is completed by releasing the pressure to the distal end plunger 202c, thereby returning the system to its initial phase 1 (FIG. 10a) condition in preparation for another cycle.

It will be seen that at the end of phase 4 (FIG. 10d), the artery is blocked on both sides of the center plunger so that the blood cannot return to the artery segment under it. However, in phase 5 (FIG. 10e) during which the impedance is measured, the pressure in the proximal end plunger 202a is released in a controlled manner, as shown in FIG. 9b, while the impedance of the skin underlying the center plunger 202b is measured via its electrodes 204, 206 to detect when the impedance starts to descend from the plateau shown in FIG. 9c. This instant of impedance change indicates the unblocking of the occluded artery such that the pressure applied by the artery to the center plunger 202b at this instant is an accurate measurement of the arterial blood pressure at this point of the blood pressure wave.

Another possible source of error in the FIGS. 1-8 embodiments is avoided in the above-described technique in that the actual impedance measurement is effected under the central plunger 202b when no mechanical maneuvers are made in it. Thus, in the techniques described above with reference to FIGS. 1-8, wherein the impedance is measured at the instant of occlusion, movement of the plunger is required to occlude the artery; however, in the technique described in FIGS. 9a–12, the impedance measurement is made at the instant of unblocking the artery effected by the release of the pressure applied by the proximal plunger 202a. At that instant, no movement is required with respect to the center plunger 202b which measures the impedance and pressure, and therefore, mechanical artefacts induced in the measurements by movement of the plunger are minimal.

Whereas a mechanical or liquid coupling is described in the techniques of FIGS. 1–8 as being preferred between the pressure generator and the pressure applicator when measuring the pressure by detecting the instant of occlusion of the artery, in the modified technique of FIGS. 9a–12, wherein the pressure is measured at the instant of unblocking of the occluded artery, it is preferred to use a gas coupling between the pressure generator and the pressure applicator. Also, whereas the impedance may be measured in both techniques by a two electrode system, it is preferable in the FIGS. 9a–12 technique to use a more elaborate electrode system providing a higher degree of sensitivity to impedance changes.

Figure 10B:
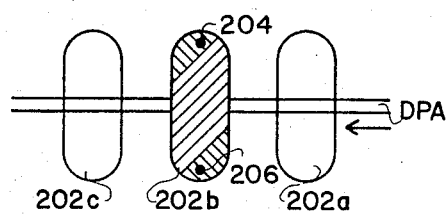
Figure 10C:
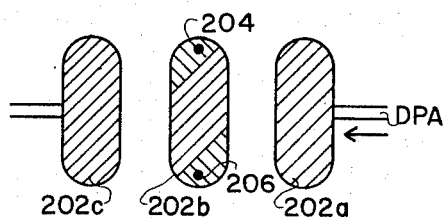
Figure 10D:
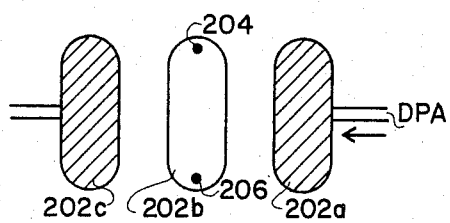
Figure 10E:
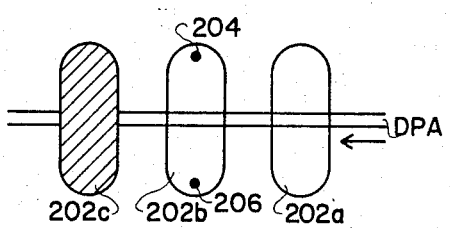
Figure 12:
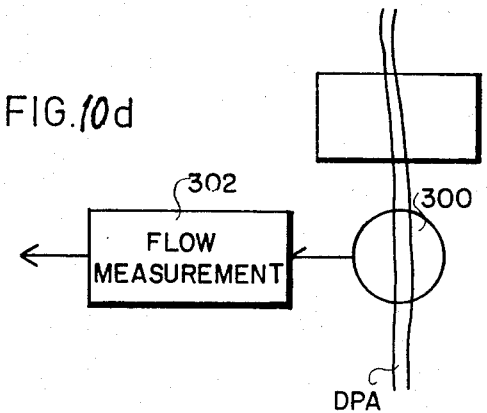
FIG. 12 is a simplified diagram illustrating another arrangement for detecting occlusion of the artery, or unblocking of the occluded artery, by monitoring blood flow by means of a Doppler device.
Figure 11:
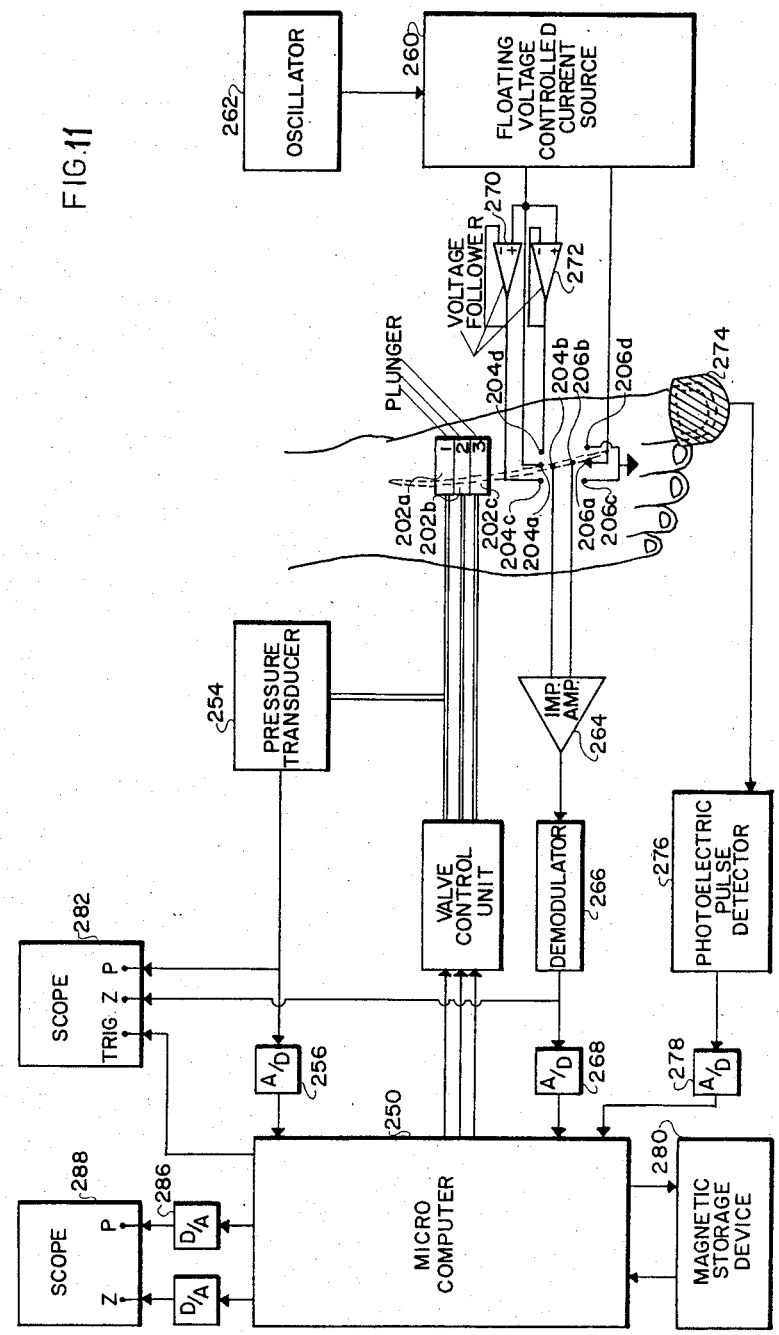
FIG. 11 is a block diagram illustrating the overall system utilizing three pressure applicators as in FIGS. 10a–10e for measuring the value of the local pressure.
Figure 13:
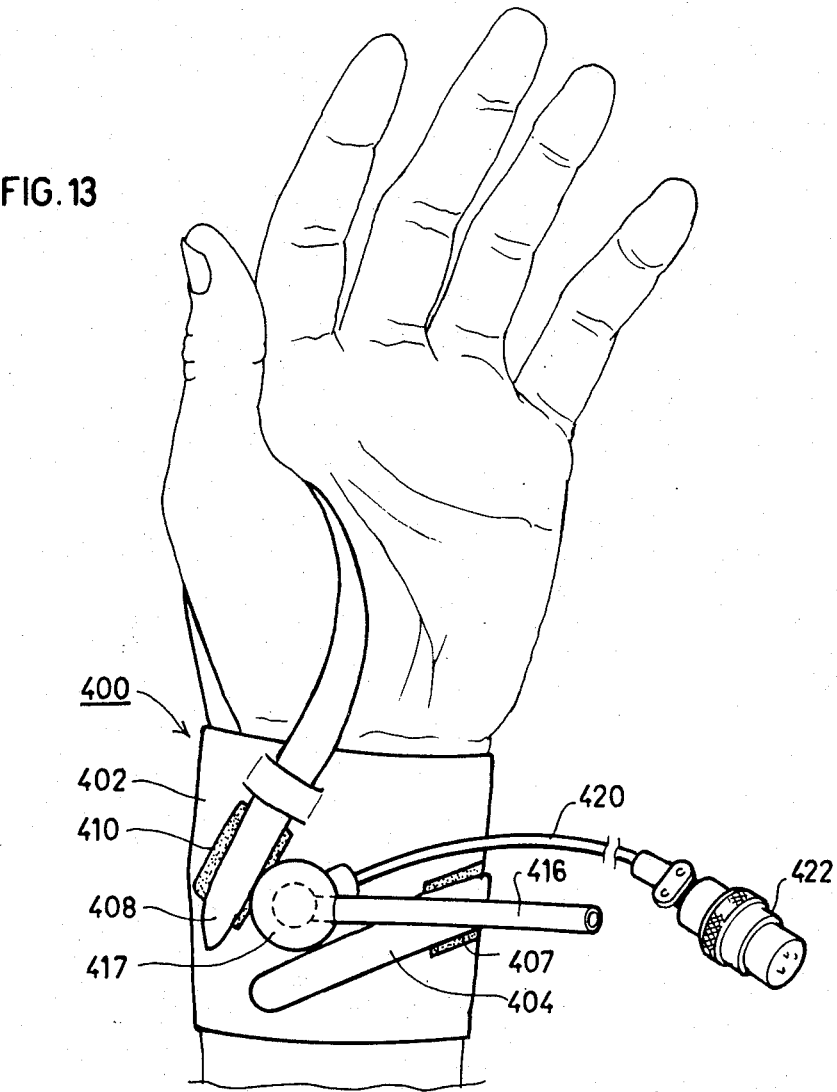
FIGS. 13–16 illustrate the pressure applying means and the detector means included in a bracelet to be applied to the subject's wrist, FIG. 12 illustrating the bracelet applied to the subject's wrist, FIG. 13 being a sectional view of FIGS. 12, FIG. 14 being a spread out bottom view of the bracelet, and FIG. 15 being a top view of the spread out bracelet.
Figure 14:
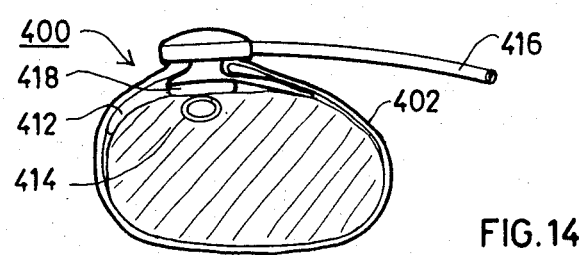
Figure 15:
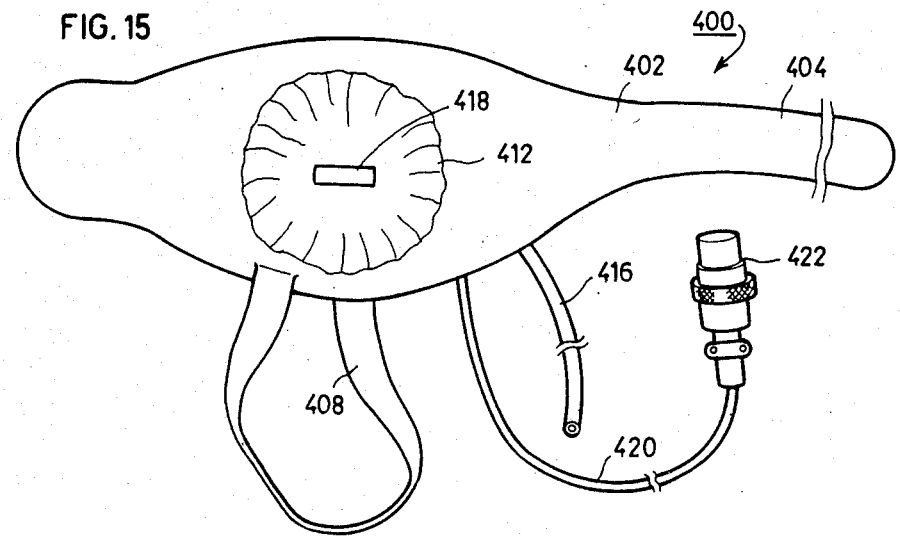
Figure 16:
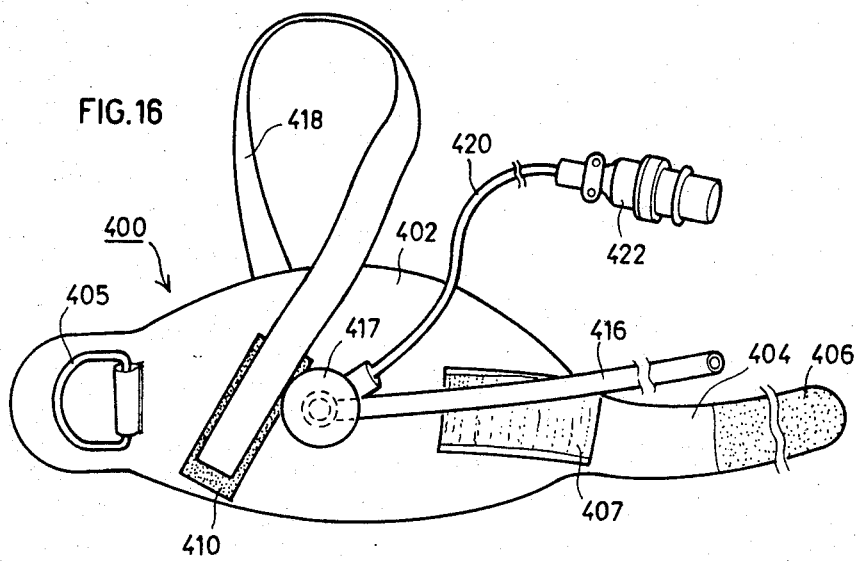

FIG. 11 is a block diagram illustrating one form of overall system which may be used with the three-plunger arrangement illustrated in FIGS. 10a–10c, and utilizing an eight-electrode arrangement for measuring impedance changes. The overall system is controlled by a microcomputer 250 and includes a valve control unit 252 which controls the application and release of the individual pressure pulses to the three plungers 202a–202c under the command of the microcomputer 250. Preferably, the plungers are air-driven under the control of valve control unit 252. The pressure underlying the central pressure plunger 202d is detected by a pressure transducer 254 which converts the pressure into electrical analog signals, the latter being converted to digital form by analog-to-digital converter 256 before being inputted into the microcomputer 250.

The illustrated eight-electrode system for measuring impedance is consituted of a first group of four electrodes 204a–204d, and a second group of four electrodes 206a–206d, as follows: Electrodes 204a and 206a are excitation or driving electrodes applied at spaced locations to the skin under examination, in this case along a short portion of the length of the artery being occluded, these electrodes being supplied with constant current from a floating voltage-controlled current source 206 driven by oscillator 262. Electrodes 204b and 206b are sensing or driven electrodes located between the two excitational electrodes, such that the constant current produces a voltage drop across them corresponding to the impedance between them, which impedance measurement is fed to the microcomputer 250 via an amplifier 264, a demodulator 266, and an analog-to-digital converter 268. Electrodes 204c and 204d, located on opposite sides of the excitational electrode 204a, act as "focussing" or "guarding" electrodes and are connected to excitational electrode 204a by voltage-follower circuits 270, 272 such that the potential of both electrodes 204c, 204d follows that of electrode 204a. Electrodes 206c and 206d are located on opposite sides of the other excitational electrodes 206a and serve a similar function with respect to it but are connected to ground.

The system illustrated in FIG. 10 further includes an optical sensor 274 applied, e.g. to the toe of the subject, which sensor is connected to a photoelectric pulse detector 276 providing synchronization pulses via an analog-to-digital converter 278 to the microcomputer 250. The microcomputer further includes outputs to scope 282, and via digital-to-analog converters 284, 286 to scope 288, for displaying the correlation between the measured pressure and impedance.

The system illustrated in FIG. 10 operates as follows: The overall system is under the control of microcomputer 250 which controls, via the value control unit 252, the application of the air pressure to the three plungers 202a–202c, e.g., according to the sequence as described above with respect to FIGS. 10a–10e. The impedance sensed by the two sensing electrodes 204b, 206b is continuously measured and amplified in amplifier 264, and is sampled by the analog-to-digital converter 268 operating under the control of microcomputer 250. The digitalization of the impedance may be continuous, but preferably begins at a predetermined point in time in the activation cycle of plungers 202a–202c, just before the pressure in the proximal plunger (202a, FIG. 10e) begins to decrease; as described above, the pressure measured at the time the impedance begins to descend from its plateau, which time indicates the instant of unblocking of the occluded artery, provides the measurement of the arterial pressure at this point of the blood pulse. Thus, microcomputer 250 is programmed to determine this point in the change of the measured impedance and to provide a measurement of the arterial pressure at this instant. This pressure may be displayed in one or both of the scopes 282, 288, and may also be stored in the magnetic storage device 280. As indicated earlier, synchronization of the individual pulses with the heartbeat is effected by the pulses from the optical sensor 274.

The sampling frequency of the analog-to-digital converter 256 may be about 1,000 Hz, which provides relatively good accuracy. Further increase in the accuracy may be obtained by zeroing, by computer command, the impedance reading just before the digitalization begins. As the measurements depend only on impedance changes and not on the absolute impedance values, the nulling does not affect the measurement.

It will thus be seen that by measuring the change in impedance, a determination is made of the instant the occluded artery is unblocked, the pressure measurement unde the central plunger 202b at this instant being thereby a measurement of the arterial pressure at this point during the pressure pulse. The above-described procedure may be repeated a plurality of times during each pressure pulse to thereby reconstruct the whole pressure wave.

Another possible sequence of activating the pressure plungers 202a, 202b, 202c (FIGS. 10a–10e) would be as follows: (a) pressurize proximal plunger 202a; (b) pressurize central plunger 202b; (c) pressurize distal plunger 202c; (d) release central plunger 202b; and (e) control the release of the proximal plunger 202b.

While a close correlation has been found to exist between the change in impedance and the instant of occlusion of the artery, or of unblocking of the occluded artery, such a correlation has also been found to exist with respect to a change in phototransmittance or photoreflectance as also described with respect to FIG. 8. Accordingly, the occlusion or unblocking of the artery can also be detected in this manner.

A further way of detecting the occulsion of the artery, or the unblocking of the occluded artery, is by detecting the change in blood flow through the artery by means of a Doppler device. This is illustrated schematically in FIG. 12, wherein a Doppler sensor 300 is applied to the artery being occluded, which sensor produces an electrical output to a flow measuring circuit 302, the latte indicating the instant the atery has been occluded by detecting the complete stoppage of flow of blood therethrough, or the instant the occluded artery has been unblocked by detecting the full flow of the blood through the previously-occluded artery.

The Embodiment of FIGS. 13-16

FIGS. 13-16 illustrate the invention including a bracelet to be worn on the wrist of the subject whose blood pressure is being measured. The bracelet, generally designated 400, includes the means for applying the individual undirectional pressure pulses, which in this case are applied to the radial artery in the subject's wrist, and also the means for detecting the condition of the radial artery. Besides bracelet 400, the apparatus includes a control unit, such as described above with respect to FIG. 11, for synchronizing the application of the pressure pulses to the subject's artery, and for measuring the instant value of the applied pressure pulse at the instant of blocking or unblocking of the artery to provide a measurement of the subject's blood pressure at that instant.

Bracelet 400 comprises a sheet 402 of strong flexible material, such as plastic or leather, adapted to be wrapped around the subject's wrist and secured in place by a strap 404 received within a ring 405 (FIG. 16) and having an underface 406 mechanically interlocking with a locking strip 407. Sliding of the band along the wrist is prevented by another strap 408 looped around the subject's thumb and interlocking with another strip 410.

An air bag 412 is secured to the underface of band 402 so as to directly overlie the subject's radial artery 414 (FIG. 14), and is inflatable by air via a feed tube 416 leading into the mouth 417 of the air bag. A sensor 418 is fixed centrally of air bag 412, as shown particularly in FIG. 15, so as to sense the condition of the artery. Sensor 418 is connected by electrical wires 420 and an electrical connector 422 to the control unit.

Air bag 412 is made of very thick plastic material and may have a diameter of 5-7 cm. Tube 416 connected to the bag passes through an opening in band 402 to the mouth of the bag. This tube is made of a flexible, non-elastic material, and leads to the control unit.

Sensor 418 may be any one of a number of different types, for example an electric impedance sensor, a pizoelectric crystal for directly sensing pressure, a Doppler flow sensor, or a photoelectric sensor, as mentioned earlier.

Preferably, the embodiment illustrated in FIGS. 13-16 uses a photoelectric sensor consisting of two parts: a light source, and a photoelectric cell (photoresistor). The light source may be either a miniature incandescent light bulb or a light emitting diode (LED). It is placed at a distance of about 2-5 mm away from the photoelectric cell; and the cell and light are placed directly over the radial artery such that the line connecting the two runs along the artery. Preferably, the photoelectric cell would be positioned distally. The sensing pair is positioned approximately at the center of the air bag (FIG. 15) and is pressed by it against the subject's skin overlying the radial artery.

This sensor detects changes in the amount of blood in the artery. When an empty artery reinflates as pressure is released, an optical change is registered by the photocell. The electrical signal thus generated is transmitted via conductors 420 to the control unit.

The control unit consists of the data acquisition system, pneumatic system, and microprocessor-based controller, as described for example in FIG. 11, which accepts the input data, activates the pneumatic system, determines the blood pressure, and displays the results.

While the invention has been described with respect to several preferred embodiments, it will be appreciated that many other variations, modifications, and applications of the invention may be made.

What is claimed is:

1. A method for the non-invasive monitoring of the arterial blood pressure of a subject, comprising the steps:

applying a plurality of discretely spaced single-polarity pressure pulses, each having a duration which is a fraction of the duration of the subject's blood pressure pulse, to a local, discrete, external point of the subject overlying an artery to effect either a blocking or unblocking condition of the artery;

detecting when said condition in the artery occurs;

and measuring the instant value of each applied pressure pulse when said condition is detected to thereby provide a measurement of the subject's blood pressure.

2. The method according to claim 1, including the further steps of:

monitoring the subject's complete arterial blood pressure pulse;

and synchronizing at least two of the applied pressure pulses to coincide with the maximum and minimum values of the subject's blood pressure pulse to thereby provide a measurement of the systolic and diastolic values of the subject's blood pressure.

3. The method according to claim 2, wherein more than two unidirectional pulses are synchronized to coincide with other points of the subject's complete arterial blood pressure pulse to thereby provide a continuous measurement of other discrete points of the subject's blood pressure.

4. The method according to claim 1, wherein said single-polarity pressure pulses are applied in a pressure-increasing direction to effect a blocking condition of the artery for a fraction of the duration of the subject's blood pressure pulse.

5. The method according to claim 1, wherein the single-polarity pulses are applied in a pressure decreasing direction to effect an unblocking condition of the artery for a fraction of the duration of the subject's blood pressure pulse.

6. A method for the non-invasive monitoring of the arterial blood pressure of a subject, comprising the steps:

applying a plurality of discretely spaced single-polarity pressure pulses, each having a duration which is a fraction of the duration of the subject's blood pressure pulse, to a local, discrete, external point of the subject overlying an artery to effect blocking of the artery;

detecting when said blocking in the artery occurs;

and measuring the instant value of each applied pressure pulse when said blocking is detected to thereby provide a measurement of the subject's blood pressure.

7. The method according to claim 6, including the further steps of:
monitoring the subject's complete arterial blood pressure pulse;
and synchronizing at least two of the applied pressure pulses to conicide with the maximum and minimum values of the subject's blood pressure pulse to thereby provide a measurement of the systolic and diastolic values of the subject's blood pressure.

8. The method according to claim 7, wherein more than two single-polarity pulses are synchronized to coincide with other points of the subject's complete arterial blood pressure pulse to thereby provide a continuous measurement of other discrete points of the subject's blood pressure.

9. A method for the non-invasive monitoring of the arterial blood pressure of a subject, comprising the steps:
applying a plurality of discretely spaced single-polarity pressure pulses, each having a duration which is a fraction of the duration of the subject's blood pressure pulse, to a local, discrete, external point of the subject overlying an artery to effect an unblocking of the artery;
detecting when said unblocking in the artery occurs;
and measuring the instant value of each applied pressure pulse when said unblocking is detected to thereby provide a measurement of the subject's blood pressure.

10. The method according to claim 9, including the further steps of:
monitoring the subject's complete arterial blood pressure pulse;
and synchronizing at least two of the applied pressure pulses to coincide with the maximum and minimum values of the subject's blood pressure pulse to thereby provide a measurement of the systolic and diastolic values of the subject's blood pressure.

11. The method according to claim 10, wherein more than two single-polarity pulses are synchronize to coincide with other points of the subject's complete arterial blood pressure pulse to thereby provide a continuous measurement of other discrete points of the subject's blood pressure.

12. Apparatus for the non-invasive monitoring of the arterial blood pressure of a subject, comprising:
pressure applying means for applying a plurality of discretely spaced single-polarity pressure pulses, each having a duration which is a fraction of the duration of the subject's blood pressure pulse, to a local, discrete, external point of the subject overlying an artery to effect either a blocking or unblocking condition of the artery;
detector means for detecting when said condition in the artery occurs;
and measuring means for measuring the instant value of each applied pressure pulse when said condition is detected to thereby provide a measurement of said subject's blood pressure.

13. The apparatus of claim 12, further comprising:
monitoring means for monitoring the subject's complete arterial blood pressure pulse;
and synchronizing means for synchronizing the application of at least two of the applied pressure pulses to coincide with the maximum and minimum values of the subject's blood pressure pulse to thereby provide a measurement of the systolic and diastolic values of the subject's blood pressure.

14. The apparatus according to claim 13, wherein said synchronizing means synchronizes the application of more than two single-polarity pulses to coincide with other points of the subject's complete arterial pulse to thereby provide a continuous measurement of other discrete points of the subject's blood pressure.

15. The apparatus according to claim 12, wherein said pressure applying means applies single-polarity pressure pulses in a pressure increasing direction to effect a blocking of the artery for a fraction of the duration of the subject's blood pressure pulse.

16. The apparatus according to claim 12, wherein said pressure applying means applies the single-polarity pressure pulses in a pressure-decreasing direction to effect an unblocking of the artery for a fraction of the duration of the subject's blood pressure pulse.

17. The apparatus according to claim 12, wherein said detector means comprises an electrical impedance detector for detecting the change in the electrical impedance of the subject's external area in the vicinity of said artery.

18. The apparatus according to claim 12, wherein said detector means comprises a Doppler device measuring blood flow to detect a change in the blood flow of said artery.

19. The apparatus according to claim 12, wherein said detector means comprises a photoelectric sensor for detecting a change in the optical characteristics of the subject's external area in the vicinity of said artery.

20. The apparatus according to claim 12, wherein said pressure applying means comprises a plurality of pressure applicators, and control means for controlling them according to a sequence minimizing shunting of the blood flow with respect to other arteries.

21. The apparatus according to claim 12, wherein said pressure applying means comprises at least three pressure applicators arranged in a line along said artery.

22. The apparatus according to claim 12, wherein said control means controls said three pressure applicators according to the following sequence, starting with the condition that the pressure to all the applicators is released;
(a) the pressure to the center applicator is applied
(b) the pressure to the two end applicators is applied;
(c) the pressure to the center applicator is released;
(d) the pressure to the end applicator proximate to the heart is released in a controlled manner while the value of the pressure at the center applicator is measured when unblocking is detected; and
(e) the pressure to the two end applicators is released.

23. The apparatus according to claim 12, further including a bracelet to be worn around the subject's wrist, said pressure applying means and said detector means being mounted on said bracelet.

24. The apparatus according to claim 23, wherein said pressure applying means comprises an inflatable air bag carried by said bracelet for applying a local pressure to the radial artery in the subject's wrist.

25. The apparatus according to claim 24, wherein said pressure detector means comprises a photoelectric sensor mounted centrally of said inflatable air bag.

26. Apparatus for the non-invasive monitoring of the arterial blood pressure of a subject, comprising:
pressure applying means for applying a plurality of discretely spaced single-polarity pressure pulses, each having a duration which is a fraction of the duration of the subject's blood pressure pulse, to a local, discrete, external point of the subject overlying an artery to effect blocking of the artery;

detector means for detecting when said blocking in the artery occurs;

and measuring means for measuring the instant value of each applied pressure pulse when said blocking is detected to thereby provide a measurement of said subject's blood pressure.

27. The apparatus of claim 26, further comprising:

monitoring means for monitoring the subject's complete arterial blood pressure pulse;

and synchronizing means for synchronizing the application of at least two of the applied pressure pulses to coincide with the maximum and minimum values of the subject's blood pressure pulse to thereby provide a measurement of the systolic and diastolic values of the subject's blood pressure.

28. The apparatus according to claim 27, wherein said synchronizing means synchronizes the application of more than two single-polarity pulses to coincide with other points of the subject's complete arterial pulse to thereby provide a continuous measurement of other discrete points of the subject's blood pressure.

29. Apparatus for the non-invasive monitoring of the arterial blood pressure of a subject, comprising:

pressure applying means for applying a plurality of discretely spaced single-polarity pressure pulses, each having a duration which is a fraction of the duration of the subject's blood pressure pulse, to a local, discrete, external point of the subject overlying an artery to effect unblocking of the artery;

detector means for detecting when said unblocking of the artery occurs;

and measuring means for measuring the instant value of each applied pressure pulse when said unblocking is detected to thereby provide a measurement of said subject's blood pressure.

30. The apparatus of claim 29, further comprising:

monitoring means for monitoring the subject's complete arterial blood pressure pulse;

and synchronizing means for synchronizing the application of at least two of the applied pressure pulses to coincide with the maximum and minimum values of the subject's blood pressure pulse to thereby provide a measurement of the systolic and diastolic values of the subject's blood pressure.

31. The apparatus according to claim 30, wherein said pressure applying means applies more than two single-polarity pulses to coincide with other points of the subject's complete arterial pulse to thereby provide a continuous measurement of other discrete points of the subject's blood pressure.

* * * * *